US012662509B2

(12) United States Patent
Lin et al.

(10) Patent No.: US 12,662,509 B2
(45) Date of Patent: Jun. 23, 2026

(54) INHIBITORS OF 17β-HSD7 AND USES THEREOF

(71) Applicant: UNIVERSITÉ LAVAL, Québec (CA)

(72) Inventors: Sheng-Xiang Lin, Québec (CA); Donald Poirier, L'Ancienne-Lorette (CA); René Maltais, Québec (CA); Jean-Yves Sancéau, Québec (CA)

(73) Assignee: ShengXiang Lin, Québec (CA)

( * ) Notice: Subject to any disclaimer, the term of this patent is extended or adjusted under 35 U.S.C. 154(b) by 370 days.

(21) Appl. No.: 18/571,556

(22) PCT Filed: Jun. 16, 2022

(86) PCT No.: PCT/CA2022/050966
§ 371 (c)(1),
(2) Date: Dec. 18, 2023

(87) PCT Pub. No.: WO2022/261774
PCT Pub. Date: Dec. 22, 2022

(65) Prior Publication Data

US 2024/0287127 A1 Aug. 29, 2024

Related U.S. Application Data

(60) Provisional application No. 63/202,568, filed on Jun. 16, 2021.

(51) Int. Cl.

| | |
|---|---|
| ***A61P 35/00*** | (2006.01) |
| ***A61K 31/58*** | (2006.01) |
| ***A61K 45/06*** | (2006.01) |
| ***C07J 73/00*** | (2006.01) |

(52) U.S. Cl.
CPC ............. *C07J 73/005* (2013.01); *A61K 31/58* (2013.01); *A61K 45/06* (2013.01); *A61P 35/00* (2018.01)

(58) Field of Classification Search
CPC ........ C07J 73/005; A61P 35/00; A61K 31/58; A61K 45/06
See application file for complete search history.

(56) References Cited

U.S. PATENT DOCUMENTS

| | | | |
|---|---|---|---|
| 4,218,446 | A | 8/1980 | Solyom et al. |
| 4,220,775 | A | 9/1980 | Rasmusson et al. |
| 4,328,221 | A | 5/1982 | Szilagyi et al. |
| 4,377,584 | A | 3/1983 | Rasmusson et al. |
| 5,693,809 | A | 12/1997 | Durette et al. |
| 5,710,275 | A | 1/1998 | Bakshi et al. |

OTHER PUBLICATIONS

Wang et al (Year: 2015).*
CRN2882942-12-1 (Year: 2023).*
Ayan et al. "Chemical synthesis, cytotoxicity, selectivity and bioavailability of 5α-androstane-3α, 17ß-diol derivatives", Bioorganic & Medicinal Chemistry, vol. 22, pp. 5847-5859, 2014.
Bellavance et al. "Potent and selective steroidal inhibitors of 17β-Hydroxysteroid dehydrogenase Type 7, an enzyme that catalyzes the reduction of key hormones estrone and dihydrotestosterone", *Journal of Medicinal Chemistry*, vol. 52, pp. 7488-7502, 2009.
International Search Report and Written Opinion issued in corresponding International application PCT/CA2022/050966 mailed Sep. 15, 2022.
Kenmogne et al. "Investigation of the In Vitro and In Vivo efficiency of RM-532-105, a 17ß-hydroxysteroid dehydrogenase type 3 inhibitor, in LAPC-4 prostate cancer cell and tumor models", *PLOS One*, pp. 1-16, 2017.
Wang et al. "Synergistic control of sex hormones by 17ß-HSD type 7: a novel target for estrogen-dependent breast cancer", *Journal of Molecular Cell Biology*, vol. 7, No. 6, pp. 568-579, 2015.
Zhang et al. "Reductive 17beta-hydroxysteroid dehydrogenases which synthesize estradiol and inactivate dihydrotestosterone constitute major and concerted players in ER+ breast cancer cells", *Journal of Steroid Biochemistry & Molecular Biology*, vol. 150, pp. 24-34, 2015.

* cited by examiner

*Primary Examiner* — Jeffrey S Lundgren
*Assistant Examiner* — Ibrahim D Bori
(74) *Attorney, Agent, or Firm* — NORTON ROSE FULBRIGHT US LLP

(57) ABSTRACT

Novel chemical agents are described herein. More specifically, a novel inhibitor of 17β-HSD7 for decreasing estradiol concentrations while restoring dihydrotestosterone (DHT) concentrations in breast cancer cells is disclosed herein. In a particular embodiment, the inhibitor of 17β-HSD7 has the following structure: (Formula I) A process for producing the novel inhibitors of 17β-HSD7 and their use in the manufacture of pharmaceutical formulations and/or combinations is also disclosed.

(I)

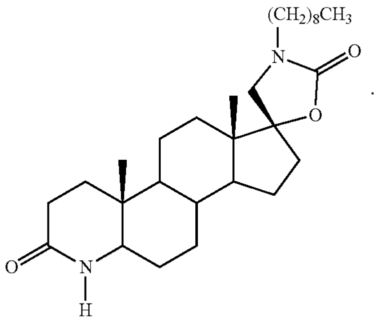

20 Claims, 7 Drawing Sheets

Figure 1:
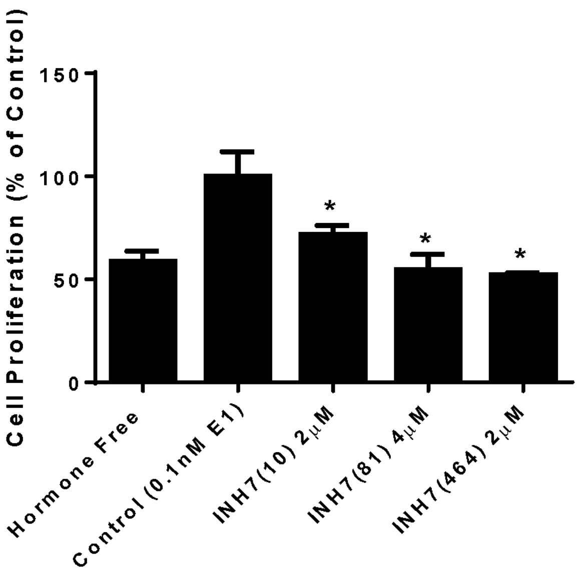

INH7(10) ($R_1 = CH_3$, $R_2$ = CHO, n = 8)
INH7(80) ($R^1$ = H, $R^2$ = CHO, n = 9)
INH7(81) ($R_1 = CH_3$, $R_2 = CH_3$, n = 6)

(A)

(B)

A

B

INHIBITORS OF 17β-HSD7 AND USES THEREOF

CROSS REFERENCE TO RELATED APPLICATIONS

This application is a national phase under 35 U.S.C. § 371 of International Application No. PCT/CA2022/050966, filed Jun. 16, 2022, which claims the benefit of U.S. Provisional Application 63/202,568, filed Jun. 16, 2021. The contents of each of the referenced applications are incorporated into the present application by reference in their entirety.

BACKGROUND

1. Field

This disclosure relates to the fields of medicine, pharmacology, chemistry and oncology. More specifically, but not exclusively, the present disclosure broadly relates to novel inhibitors of human 17β-HSD7. Yet more specifically, but not exclusively, the present disclosure broadly relates to novel inhibitors of 17β-HSD7 capable of decreasing estradiol concentrations while restoring dihydrotestosterone (DHT) concentrations in breast cancer cells. In particular, a novel inhibitor of 17β-HSD7, compositions comprising same and methods of treatment are disclosed.

2. Related Art

Breast cancer (BC) is the most commonly diagnosed cancer and the second highest cause of cancer-related death in females worldwide. A large proportion of BCs are initially estrogen-dependent; these account for 60% of BC cases in premenopausal women and 75% of cases in postmenopausal women. In the latter, ovarian-derived estrogens are dramatically decreased and replaced by estrogens synthesized by steroidogenic enzymes from precursor steroids in an intracrine manner. The most potent estrogen, estradiol (E2), which is formed by the reduction of estrone (E1) and/or by the aromatization of testosterone (T), serves a dual role in BC as a hormone stimulating cell proliferation through binding to estrogen receptors (ERs), as well as a pro-carcinogen inducing genetic damage and mutations.

Consequently, blockage of E2 production with specific inhibitors of steroidogenic enzymes such as aromatase inhibitors (AIs) comprises one of the two currently available standard therapies. The other approach involves blocking the ER with selective estrogen receptor modulators (SERMs).

In contrast to E2, which predominantly contributes to breast carcinoma growth through ER, the non-aromatic androgen, dihydrotestosterone (DHT), has recently been reported to exert anti-proliferative effects via the androgen receptor (AR) by activating $p21^{waf1/cip1}$ and/or inhibiting cyclin D1. Indeed, the AR is expressed in ~80% of primary BCs, which is greater than the proportion expressing ER (70%).

A systematic meta-analysis has demonstrated that co-expression of ARs in female breast tumors is associated with a better prognosis and outcome. Moreover, metabolites of DHT such as 5α-androstane-3β,17β-diol (3β-diol) were shown to display weak estrogenic potency toward MCF-7 cells through binding to ER, which was thought to be a possible mechanism for inducing aromatase inhibitor (AI) resistance. Therefore, a new concept for the treatment of BC has emerged through the joint targeting of E2 (reduction) and DHT (restoration).

The intracrine pathways for estrogen synthesis include: (i) the "aromatase pathway", which transforms androgens into estrogens; and (ii) the "sulfatase pathway", which desulfates dehydroepiandrosterone-sulfate (DHEA-S) and estrone-sulfate (E1-S) followed by the action of reductive 17β-HSD1 and 17β-HSD7 that are integrated into both pathways converting E1 into potent E2. Therefore, aromatase, steroid sulfatase (STS), and reductive 17β-HSDs involved in the final steps of E2 biosynthesis are primary targets for blocking E2 production.

Aromatase inhibitors have been used in the clinic with favorable outcomes; however, resistance to AIs has become an inevitable occurrence. Thus, approaches targeting other enzymes could be effective at reducing estrogen synthesis. 17β-HSD1 has been accepted as a critical therapeutic target to block E2 production. Structure-based studies suggested that 17β-HSD1 alternatively binds to and inactivates DHT, providing a basis for the dual catalytic function by this long-held "estrogenic enzyme". Another dual functional enzyme, 17β-HSD7, also converts E1 into E2 and catalyzes a marked inactivation of DHT into the weak estrogen, 3p3-diol.

Expression of human 17β-HSD7 has been reported in the ovary, placenta, mammary gland, liver, and brain. At present, it is generally accepted that 17β-HSD7 is primarily involved in cholesterol synthesis rather than in steroidogenesis. This has had a marked effect on the direction of studies involving this enzyme and explains the limited number of studies addressing its function in steroid hormone biosynthesis and related diseases including BC. 17β-HSD7 was first detected as a prolactin receptor-associated protein in rat. Detection of a high expression level in the corpus *luteum* of pregnant mice supported the assumption of its role in E2 synthesis. The predominant involvement of 17β-HSD7 in cholesterol metabolism rather than in sex steroid synthesis, was further supported by the observation that although 17β-HSD7 knockout mice were fertile, they bred nonviable fetuses due to defective in situ cholesterol biosynthesis in the brain.

SUMMARY

The present disclosure broadly relates to novel inhibitors of 17β-HSD7. More specifically, but not exclusively, the present disclosure relates to novel inhibitors of 17β-HSD7 capable of decreasing estradiol concentrations while restoring dihydrotestosterone (DHT) concentrations in breast cancer cells. The present disclosure also relates to the synthesis of inhibitors of 17β-HSD7. Moreover, the present disclosure relates to compositions and pharmaceutical formulations comprising an inhibitor of 17β-HSD7. Yet moreover, the present disclosure relates to compositions and pharmaceutical formulations comprising an inhibitor of 17β-HSD7 for decreasing estradiol concentrations, while restoring dihydrotestosterone (DHT) concentrations in breast cancer cells. Furthermore, the present disclosure relates to methods of treatment comprising the use of an inhibitor of 17β-HSD7. Yet furthermore, the present disclosure relates to methods of treatment comprising the use of an inhibitor of 17β-HSD7 for decreasing estradiol concentrations, while restoring dihydrotestosterone (DHT) concentrations in breast cancer cells.

In an aspect, the present disclosure relates to an inhibitor of 17β-HSD7 having the structure of Formula I:

Formula I

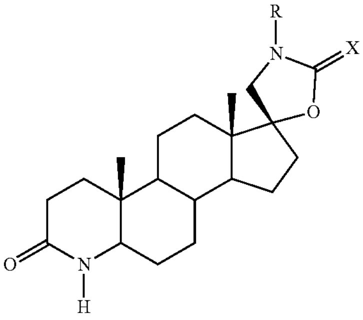

wherein R is $alkyl_{(C\leq 12)}$ or $cycloalkyl_{(C\leq 12)}$; and X is O or S; or a pharmaceutically acceptable salt, prodrug or solvate thereof.

In an embodiment, the 17β-HSD7 inhibitor of Formula I has the structure:

INH7-464

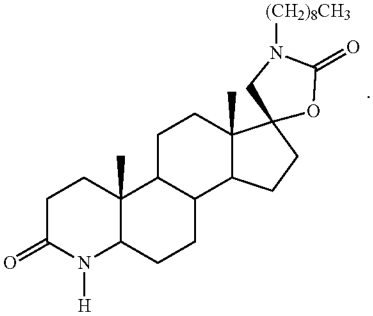

In an aspect, the present disclosure relates to a pharmaceutical composition comprising a pharmaceutically acceptable amount of a 17 β-HSD7 inhibitor such as disclosed herein, or a pharmaceutically acceptable salt, prodrug, or solvate thereof, and a pharmaceutically acceptable carrier.

In an aspect, the present disclosure relates to the use of a 17 β-HSD7 inhibitor such as disclosed herein, or a pharmaceutically acceptable salt, prodrug, or solvate thereof, for the prophylaxis or treatment of a disease. In an embodiment of the present disclosure, the disease is associated with uncontrolled cell growth, proliferation and/or survival. In a further embodiment of the present disclosure, the disease comprises breast cancer.

In an aspect, the present disclosure relates to the use of a pharmaceutical composition comprising a pharmaceutically acceptable amount of a 17 β-HSD7 inhibitor such as disclosed herein, or a pharmaceutically acceptable salt, prodrug, or solvate thereof, and a pharmaceutically acceptable carrier for the prophylaxis or treatment of a disease. In an embodiment of the present disclosure, the disease is associated with uncontrolled cell growth, proliferation and/or survival. In a further embodiment of the present disclosure, the disease comprises breast cancer.

In an aspect, the present disclosure relates to a method of treating a disease in a subject comprising administering to the subject a 17 β-HSD7 inhibitor such as disclosed herein or a pharmaceutically acceptable salt, prodrug, or a solvate thereof. In an embodiment of the present disclosure, the 17 β-HSD7 inhibitor, or a pharmaceutically acceptable salt, prodrug, or solvate thereof, is administered intravenously, intra-arterially, subcutaneously, topically, or intramuscularly. In an embodiment of the present disclosure, the 17 β-HSD7 inhibitor, or a pharmaceutically acceptable salt, prodrug, or solvate thereof, is administered systemically, regionally to a tumor/disease site, locally to a tumor/disease site, into tumor/tissue vasculature or intratumorally. In a further embodiment of the present disclosure, the disease is associated with uncontrolled cell growth, proliferation and/or survival. In a further embodiment of the present disclosure, the disease comprises breast cancer. In yet a further embodiment of the present disclosure, the subject is a human. In yet a further embodiment of the present disclosure, the subject is a non-human animal.

In aspect, the present disclosure relates to a method of reducing proliferation of/or inducing cell death of neoplastic cells comprising, contacting the neoplastic cells with one or more of the 17 β-HSD7 inhibitors as disclosed herein, or a pharmaceutically acceptable salt, prodrug, or solvate thereof.

In an aspect, the present disclosure relates to the use of one or more of the 17 β-HSD7 inhibitors as disclosed herein, or a pharmaceutically acceptable salt, prodrug, or solvate thereof, in the manufacture of a medicament for the treatment of a disease associated with uncontrolled cell growth, proliferation and/or survival. In a further embodiment of the present disclosure, the disease comprises breast cancer.

In an aspect, the present disclosure relates to a pharmaceutical composition comprising an effective amount of one or more of the 17 β-HSD7 inhibitors as disclosed herein, or a pharmaceutically acceptable salt, prodrug, or solvate thereof, in association with one or more pharmaceutically acceptable carriers, excipients or diluents.

In an aspect, the present disclosure relates to an admixture comprising an effective amount of one or more of the 17 β-HSD7 inhibitors as disclosed herein, or a pharmaceutically acceptable salt, prodrug, or solvate thereof, in association with one or more pharmaceutically acceptable carriers, excipients or diluents.

It is contemplated that any embodiment discussed in this specification can be implemented with respect to any method or composition discussed in this specification, and vice versa. Furthermore, it is contemplated that the compositions and kits discussed in this specification can be used to achieve the methods discussed in this specification, and vice versa.

Disclosed in the context of the present disclosure are embodiments 1 to 25. Embodiment 1 is an inhibitor of 17β-HSD7, wherein the inhibitor has the structure of Formula I:

Formula I

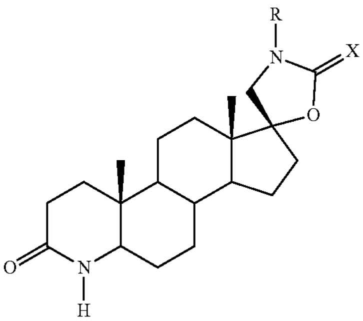

wherein R is alkyl$_{(C\leq 12)}$ or cycloalkyl$_{(C\leq 12)}$; and X is O or S; or a pharmaceutically acceptable salt, prodrug or solvate thereof.

Embodiment 2 is the inhibitor of embodiment 1, having the structure:

INH7-464

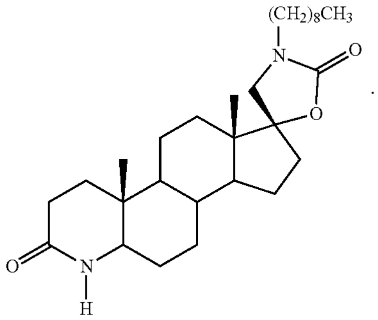

Embodiment 3 is a method of treating cancer in a subject, the method comprising administering to the subject the inhibitor of embodiments 1 or 2.

Embodiment 4 is the method of embodiment 3, wherein the cancer is an estrogen-sensitive cancer.

Embodiment 5 is the method of embodiment 4, wherein the cancer is breast cancer.

Embodiment 6 is the method of embodiment 5, wherein the inhibitor is the inhibitor of embodiment 2.

Embodiment 7 is the method of embodiment 3, further comprising treating the subject with a secondary cancer therapy.

Embodiment 8 is the method of embodiment 6, further comprising treating the subject with a secondary cancer therapy.

Embodiment 9 is the method of embodiment 7 or 8, wherein the secondary cancer therapy is selected from the group consisting of chemotherapy, toxin therapy, radiation therapy, hormone or anti-hormone therapy, surgery, cryotherapy, or immunotherapy.

Embodiment 10 is the method of any one of embodiments 3 to 9, further comprising administering the inhibitor at least a second time.

Embodiment 11 is the method of any one of embodiments 3 to 9, wherein the inhibitor is administered intravenously, intra-arterially, subcutaneously, topically, or intramuscularly.

Embodiment 12 is the method of any one of embodiments 3 to 9, wherein the inhibitor is administered systemically, regionally to a tumor/disease site, locally to a tumor/disease site, into tumor/tissue vasculature or intratumorally.

Embodiment 13 is the method of any one of embodiments 3 to 12, wherein the cancer is multi drug resistant.

Embodiment 14 is the method of any one of embodiments 3 to 12, wherein the cancer is metastatic.

Embodiment 15 is the method of any one of embodiments 3 to 12, wherein the cancer is recurrent.

Embodiment 16 is the method of any one of embodiments 3 to 12, wherein treating comprises inhibiting cancer growth, killing cancer cells, reducing tumor burden, reducing tumor size, improving said subject's quality of life or prolonging said subject's length of life.

Embodiment 17 is the method of any one of embodiments 3 to 16, wherein the subject is a human.

Embodiment 18 is the method of any one of embodiments 3 to 16, wherein the subject is a non-human animal.

Embodiment 19 is a pharmaceutical composition comprising a pharmaceutically acceptable amount of the inhibitor according to embodiment 1 or 2 and a pharmaceutically acceptable carrier.

Embodiment 20 is the use of the inhibitor according to embodiment 1 or 2 for the prophylaxis or treatment of a disease.

Embodiment 21 is the use of embodiment 20, wherein the disease is associated with uncontrolled cell growth, proliferation and/or survival.

Embodiment 22 is the use of embodiment 21, wherein the disease comprises breast cancer.

Embodiment 23 is the use of the pharmaceutical composition of embodiment 19 for the prophylaxis or treatment of a disease.

Embodiment 24 is the use of embodiment 23, wherein the disease is associated with uncontrolled cell growth, proliferation and/or survival.

Embodiment 25 is the use of embodiment 24, wherein the disease comprises breast cancer.

The word "a" or "an" when used in conjunction with the term "comprising" in the claims and/or the specification may mean "one", but it is also consistent with the meaning of "one or more", "at least one", and "one or more than one" unless the content clearly dictates otherwise. Similarly, the word "another" may mean at least a second or more unless the content clearly dictates otherwise.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this specification and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The foregoing and other advantages and features of the present disclosure will become more apparent upon reading of the following non-restrictive detailed description of illustrative embodiments thereof, with reference to the accompanying drawings/figures. It should be understood, however, that the detailed description and the illustrative embodiments, while indicating specific embodiments of the disclosure, are given by way of illustration only, since various changes and modifications within the spirit and scope of the disclosure will become apparent to those skilled in the art from this description.

BRIEF DESCRIPTION OF THE DRAWINGS/FIGURES

The following figures/drawings form part of the present specification and are included to further demonstrate certain aspects of the present specification. The present specification may be better understood by reference to one or more of these figures/drawings in combination with the detailed description. In the appended drawings/figures:

FIG. 1—is an illustration of the effect of various inhibitors of 17β-HSD1 (INH7-10, INH7-81 and INH7-464) on MCF-7 cell proliferation over a period of 144 hours.

Figure 2:
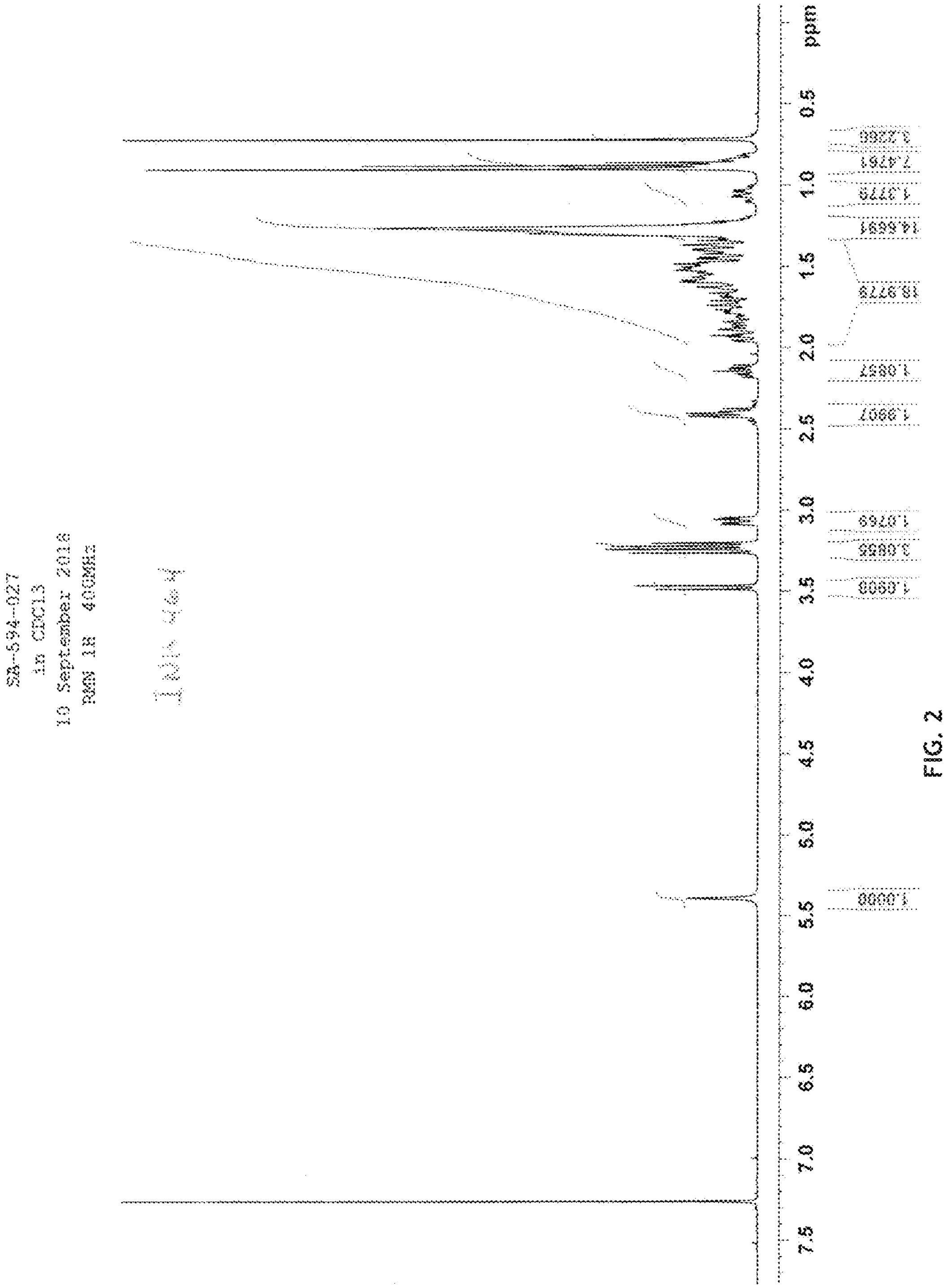

FIG. 2—is an $^1H$ NMR spectrum of INH7-464.

Figure 3:
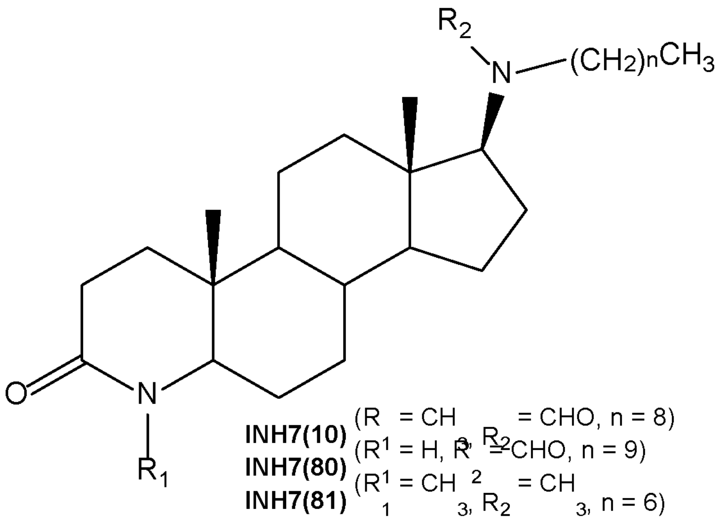

FIG. 3—is an illustration of the chemical structures for 17β-HSD7 inhibitors INH7(10), INH7(80) and INH7(81).

Figure 4:
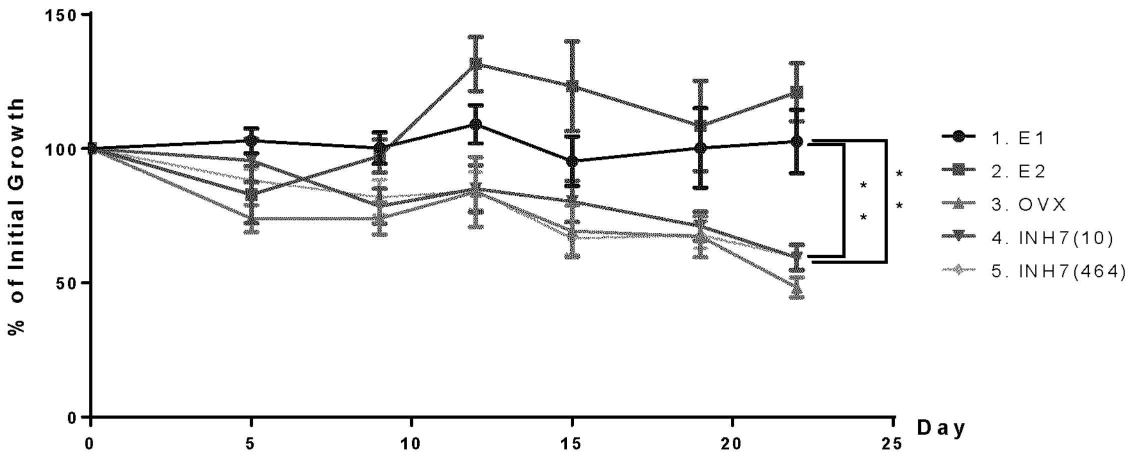

FIG. 4—is an illustration of the effect of various inhibitors of 17 β-HSD1 (INH7-10 and INH7-464) on the growth of human MCF-7 breast tumors in nude mice over a period of 22 days; illustration of the regression of MCF-7 xenograft tumor growth in OVX nude mice (cf. Table 1). The growth regression curves represent the decrease in tumor volume in response to INH7 (INH7-10 and INH7-464) treatment (Groups 4 and 5). Group 1 Control: E1 0.1 μg/mice/day; Group 2: E2 0.1 μg/mice/day; Group 3: OVX (Group of mice having had an ovariectomy); Group 4: E1 0.1 μg/mice/day; INH7(10) 5 mg/kg/day; Group 5: E1 0.1 μg/mice/day; INH7(464) 5 mg/kg/day. Tumor volume=0.52×(length×width$^2$). Statistical significance by one-way ANOVA assay is shown by **P<0.01.

Figure 5:
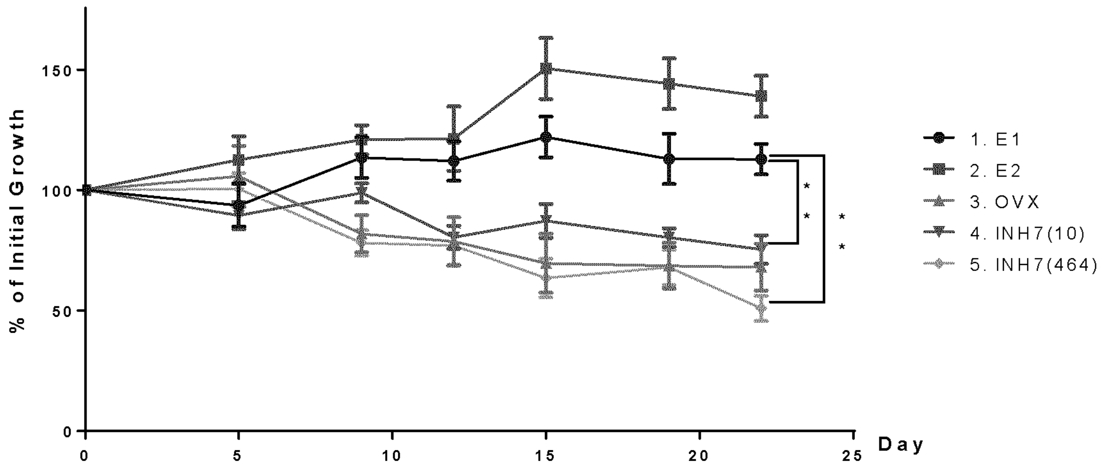

FIG. 5—is an illustration of the effect of various inhibitors of 17 β-HSD1 (INH7-10 and INH7-464) on the growth of human T47D breast tumors in nude mice over a period of 22 days; illustration of the regression of T47D xenograft tumor growth in OVX nude mice by (cf. Table 2). The growth regression curves represent the decrease in tumor volume in response to INH7 (INH7-10 and INH7-464) treatment (Groups 4 and 5). Group 1 Control: E1 0.1 μg/mice/day; Group 2: E2 0.1 μg/mice/day; Group 3: OVX (Group of mice having had an ovariectomy); Group 4: E1 0.1 μg/mice/day; INH7(10) 5 mg/kg/day; Group 5: E1 0.1 μg/mice/day; INH7(464) 5 mg/kg/day. Statistical significance by one-way ANOVA assay is shown by **P<0.01.

Figure 6:
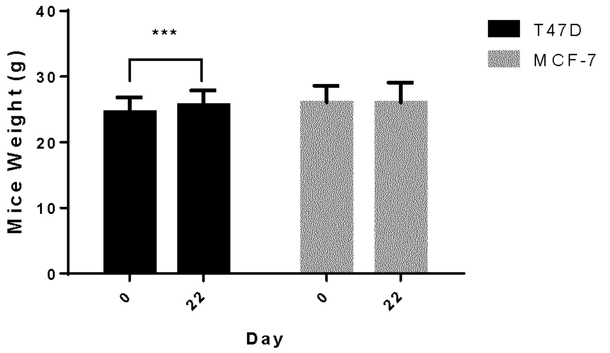
Figure 6:
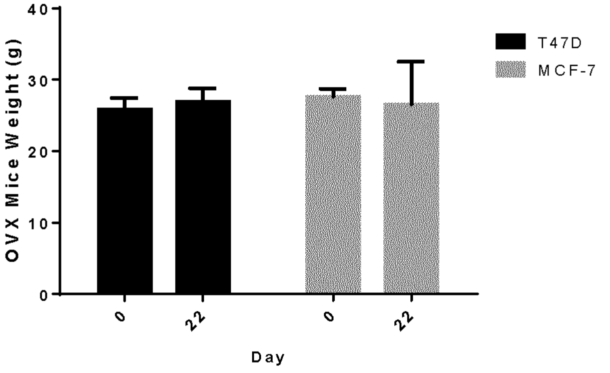

FIG. 6A—is an illustration of the body weight of the nude mice following treatment of human MCF-7 and T47D breast tumors with INH7-47 over a period of 22 days. The absence of weight loss, if any, is indicative of the non-toxicity of the INH-47 (INH7-10 and INH7-464) inhibitors. (FIG. 6B) is an illustration of the body weight of the OVX nude mice (mice having undergone an ovariectomy) over a period of 22 days. The OVX mice were not treated with an INH7 inhibitor, but instead were subjected to daily subcutaneous (s.c.) injection with vehicle (0.4% methylcellulose/DMSO (92/8)).

Figure 7:
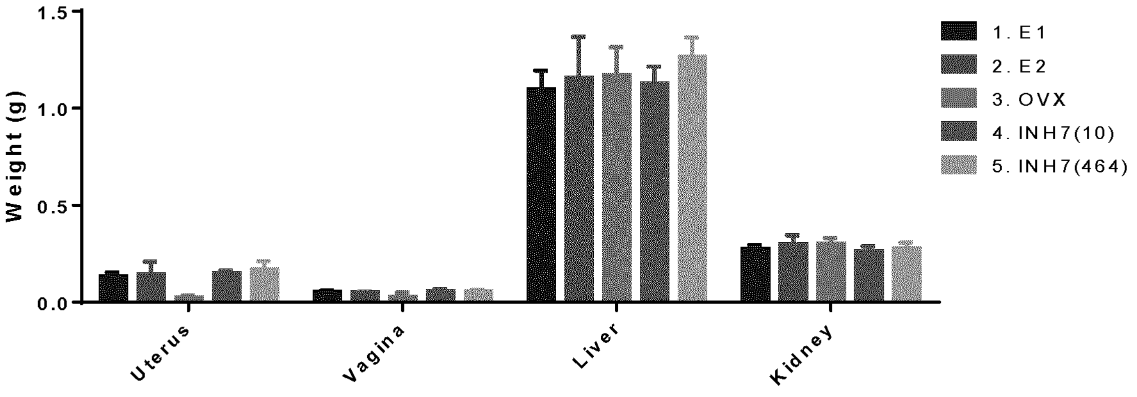

FIG. 7—is an illustration of the uterus, vagina, liver and kidney weight following treatment of human T47D breast tumors with various inhibitors of 17 β-HSD1 (INH7-10 and INH7-464) in nude mice over a period of 22 days.

Figure 8:
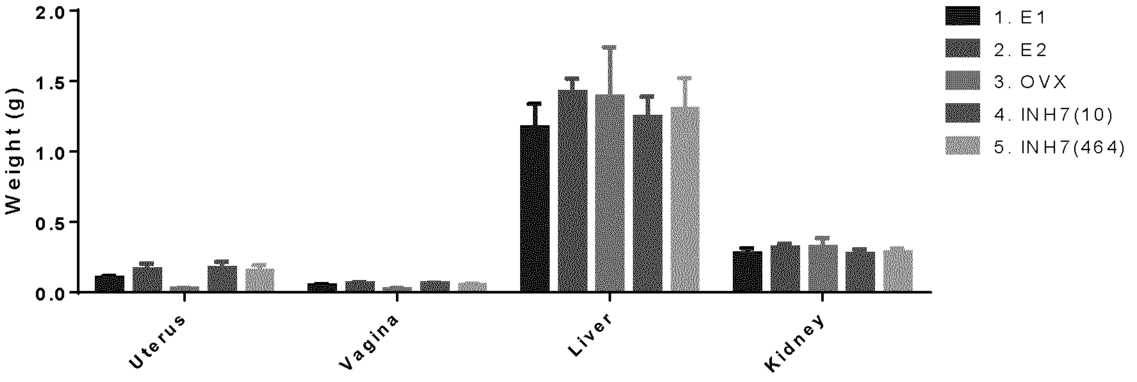

FIG. 8—is an illustration of the uterus, vagina, liver and kidney weight following treatment of human MCF-7 breast tumors with various inhibitors of 17 β-HSD1 (INH7-10 and INH7-464) in nude mice over a period of 22 days.

Figure 9:
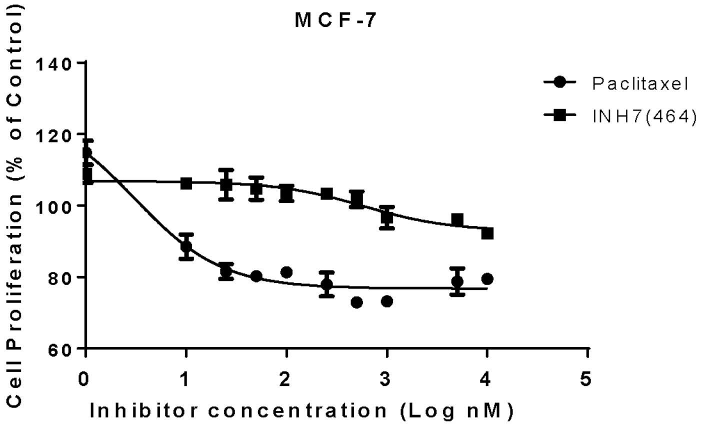
Figure 9:
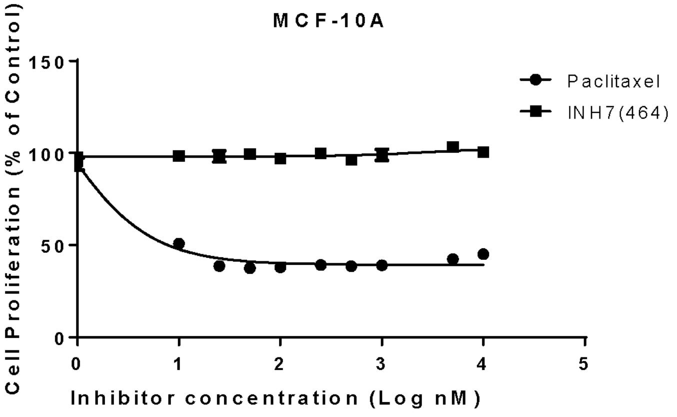

FIG. 9A—is an illustration of the cytotoxicity of the INH7-464 inhibitor on the MCF-7 cell line. FIG. 9B—is an illustration of the cytotoxicity of the INH7-464 inhibitor on the MCF-10A cell line. Paclitaxel (PTX) was used as the reference compound and was dissolved in DMSO for the stock solutions. The stock solutions were subsequently diluted at multiple concentrations with culture media in order to obtain the final desired concentrations ranging between 1 nM-100 μM. The incubation time was 3 days. The $IC_{50}$ values (at which 50% of cell growth inhibition—concentration that inhibits 50% of cell proliferation—is observed) were calculated using an iterative least square regression method (cf. Table 3). The cytotoxicity values for the INH7-464 inhibitor were lower than those for Paclitaxel (PTX) in the different cell lines (cf. Table 3).

Figure 10:
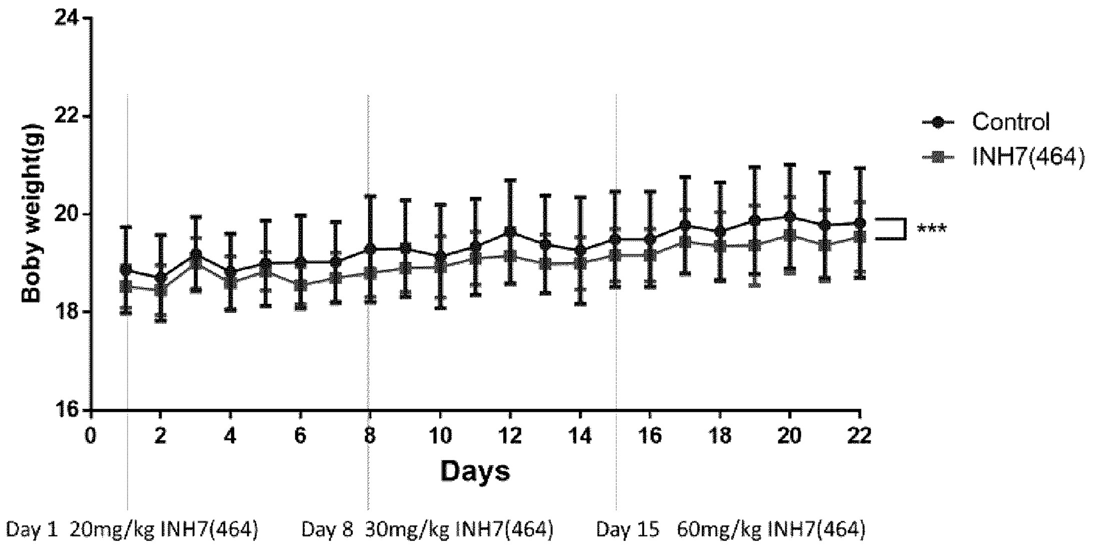

FIG. 10—is an illustration of the toxicity of the INH7-464 inhibitor in mice (8 mice/group) at various concentrations over a period of 21 days. Control Group: 0.4% methylcellulose/DMSO (92/8). INH7-464 group: Day 1: 20 mg/kg (INH7-464); Day 8: 30 mg/kg (INH7-464); Day 15: 60 mg/kg (INH7-464). INH7-464 was observed to be very well tolerated after weekly subcutaneous injection (s.c.) administration (20-60 mg/kg for 3 weeks), there being no apparent toxicity at 60 mg/day/mouse (s.c.). Statistical significance by T-test is shown by ***P<0.001.

Figure 11:
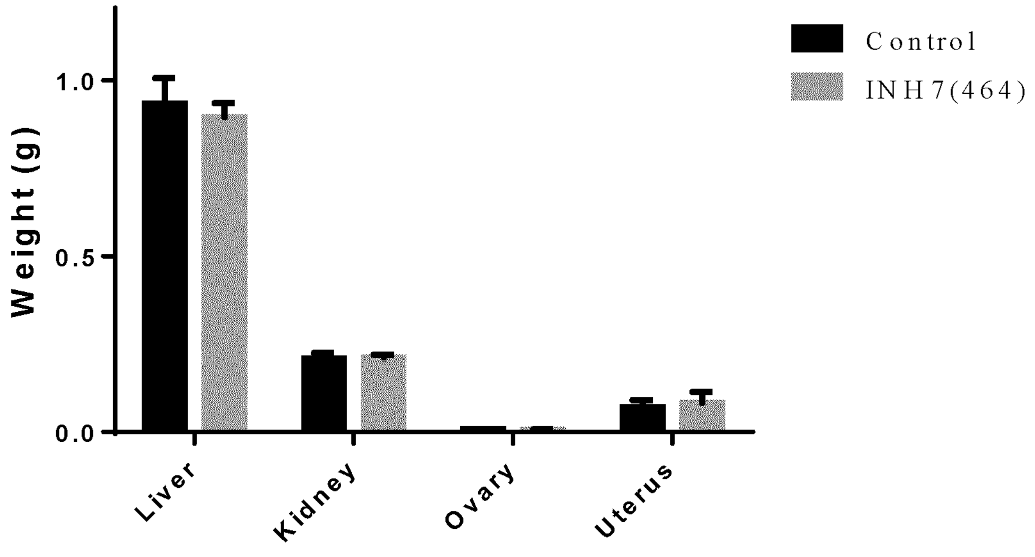

FIG. 11—is an illustration of the effect (toxicity) of the INH7-464 inhibitor on the liver, kidney, ovary and uterus weight, as per the toxicity experiment illustrated in FIG. 10. The absence of weight loss, if any, is indicative of the non-toxicity of the INH7-464 inhibitor.

DETAILED DESCRIPTION OF ILLUSTRATIVE EMBODIMENTS

The present disclosure relates to novel inhibitors of 17β-HSD7. More specifically, but not exclusively, the present disclosure relates to novel inhibitors of 17β-HSD7 capable of decreasing estradiol concentrations while restoring dihydrotestosterone (DHT) concentrations in breast cancer cells. The present disclosure also relates to the synthesis of inhibitors of 17β-HSD7. Moreover, the present disclosure relates to compositions and pharmaceutical formulations comprising an inhibitor of 17β-HSD7. Yet moreover, the present disclosure relates to compositions and pharmaceutical formulations comprising an inhibitor of 17β-HSD7 for decreasing estradiol concentrations, while restoring dihydrotestosterone (DHT) concentrations in breast cancer cells. Furthermore, the present disclosure relates to methods of treatment comprising the use of an inhibitor of 17β-HSD7. Yet furthermore, the present disclosure relates to methods of treatment comprising the use of an inhibitor of 17β-HSD7 for decreasing estradiol concentrations, while restoring dihydrotestosterone (DHT) concentrations in breast cancer cells.

In a particular aspect, the present disclosure relates to an inhibitor of 17β-HSD7 having the structure of Formula I:

Formula I

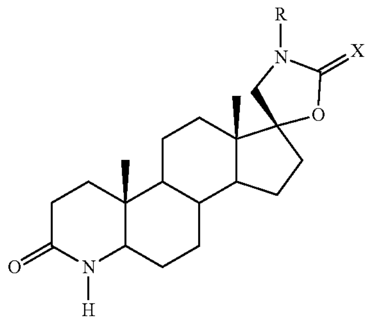

wherein R is $alkyl_{(C\leq12)}$ or $cycloalkyl_{(C\leq12)}$; and X is O or S; or a pharmaceutically acceptable salt, prodrug or solvate thereof.

In a further particular aspect, the present disclosure relates to an inhibitor of 17β-HSD7 having the structure:

INH7-464

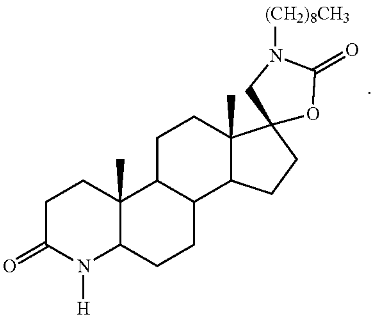

These and other aspects of the disclosure are described in greater detail below.

The 17β-HSD7 inhibitors of the present disclosure are shown, for example, above in the summary section and in the examples and claims below. INH7-464 can be synthesized according to the methods described, for example, in the Examples section below.

Atoms making up INH7-464 and other 17β-HSD7 inhibitors of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

INH7-464, and other 17β-HSD7 inhibitors of the present disclosure may also exist in prodrug form. Since prodrugs are known to enhance numerous desirable qualities of pharmaceuticals (e.g., solubility, bioavailability, manufacturing, etc.), INH7-464 may, if desired, be delivered in prodrug form. Thus, the disclosure contemplates prodrugs of the 17β-HSD7 inhibitors of the present disclosure. Prodrugs of INH7-464, and other 17β-HSD7 inhibitors of the present disclosure may be prepared by modifying functional groups present in the compound in such a way that the modifications are cleaved, either in routine manipulation or in vivo, to the parent compound. Accordingly, prodrugs include, for example, compounds described herein in which an amino, or carboxy group is bonded to any group that, when the prodrug is administered to a subject, cleaves to form an amino, or carboxy, respectively.

It should be recognized that the particular anion or cation forming a part of any salt form of INH7-464, or any other 17β-HSD7 inhibitor of the present disclosure is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

Those skilled in the art of organic chemistry will appreciate that many organic compounds can form complexes with solvents in which they are reacted or from which they are precipitated or crystallized. These complexes are known as "solvates." For example, a complex with water is known as a "hydrate." Solvates of INH7-464, or any other 17β-HSD7 inhibitor of the present disclosure are within the scope of the present disclosure. It will also be appreciated by those skilled in organic chemistry that many organic compounds can exist in more than one crystalline form. For example, crystalline forms may vary from solvate to solvate. Thus, all crystalline forms of INH7-464, or any other 17β-HSD7 inhibitor of the present disclosure or the pharmaceutically acceptable solvates thereof are within the scope of the present disclosure.

Synthetic Methods

In some aspects, INH7-464, or any other 17β-HSD7 inhibitor of the present disclosure can be synthesized using the methods of organic chemistry as described in this application. These methods can be further modified and optimized using the principles and techniques of organic chemistry as applied by a person skilled in the art. Such principles and techniques are taught, for example, in *March's Advanced Organic Chemistry: Reactions, Mechanisms, and Structure* (2007), which is incorporated by reference herein.

Process Scale-Up

The synthetic methods described herein can be further modified and optimized for preparative, pilot- or large-scale production, using the principles and techniques of process chemistry as applied by a person skilled in the art. Such principles and techniques are taught, for example, in *Practical Process Research & Development* (2000), which is incorporated by reference herein. The synthetic method described herein may be used to produce preparative scale amounts of INH7-464, or any other 17β-HSD7 inhibitor of the present disclosure.

Chemical Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —$CO_2$H); "halo" means independently —F, —Cl, —Br or —I; "amino" means —$NH_2$; "hydroxyamino" means —NHOH; "nitro" means —$NO_2$; "imino" means =NH; "cyano" means —CN; "isocyanate" means —N=C=O; "azido" means —$N_3$; in a monovalent context "phosphate" means —OP(O)$(OH)_2$ or a deprotonated form thereof; in a divalent context "phosphate" means —OP(O)(OH)O— or a deprotonated form thereof; "mercapto" means —SH; and "thio" means =S; "sulfato" means —$SO_3$H, "sulfamido" means —$S(O)_2NH_2$, "sulfonyl" means —$S(O)_2$—; and "sulfinyl" means —S(O)—.

In the context of chemical formulas, the symbol "—" means a single bond, "=" means a double bond, and "≡" means a triple bond. The symbol "----" represents an optional bond, which if present is either single or double. The symbol "⩦" represents a single bond or a double bond. Any undefined valency on an atom of a structure shown in this application implicitly represents a hydrogen atom bonded to that atom.

The term "alkyl" as used herein, represents a monovalent group derived from a straight or branched chain saturated hydrocarbon comprising, unless otherwise specified, from 1 to 12 carbon atoms and is exemplified by methyl, ethyl, n- and iso-propyl, n-, sec-, iso- and tert-butyl, neopentyl, nonyl and the like and may be optionally substituted with one, two, three or more substituents.

The term "cycloalkyl" as used herein, represents a monovalent saturated or unsaturated non-aromatic cyclic hydrocarbon group of three to 12 carbon atoms, unless otherwise specified, and is exemplified by cyclopropyl, cyclobutyl, cyclopentyl, cyclohexyl, cycloheptyl, bicyclo[2.2.1.]heptyl and the like. The cycloalkyl groups of the present disclosure can be optionally substituted.

An "alkane" or "cycloalkane" refers to the compound H—R, wherein R is alkyl or cycloalkyl as these terms are defined above. When any of these terms is used with the "substituted" modifier one or more hydrogen atoms have been independently replaced by a group, non-limiting examples of which include. —OH, —F, —Cl, —Br, —I, $—NH_2$, $—NO_2$, $—CO_2H$, $—CO_2CH_3$, —CN, —SH, $—OCH_3$, $—OCH_2CH_3$, $—C(O)CH_3$, $—NHCH_3$, $—NHCH_2CH_3$, $—N(CH_3)_2$, $—C(O)NH_2$, $—OC(O)CH_3$, or $—S(O)_2NH_2$. The following groups are non-limiting examples of substituted alkyl groups: $—CH_2OH$, $—CH_2Cl$, $—CF_3$, $—CH_2CN$, $—CH_2C(O)OH$, $—CH_2C(O)OCH_3$, $—CH_2C(O)NH_2$, $—CH_2C(O)CH_3$, $—CH_2OCH_3$, $—CH_2OC(O)CH_3$, $—CH_2NH_2$, $—CH_2N(CH_3)_2$, and $—CH_2CH_2Cl$.

EXAMPLES

The following examples are included to demonstrate preferred embodiments of the disclosure. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Synthesis of INH7-464

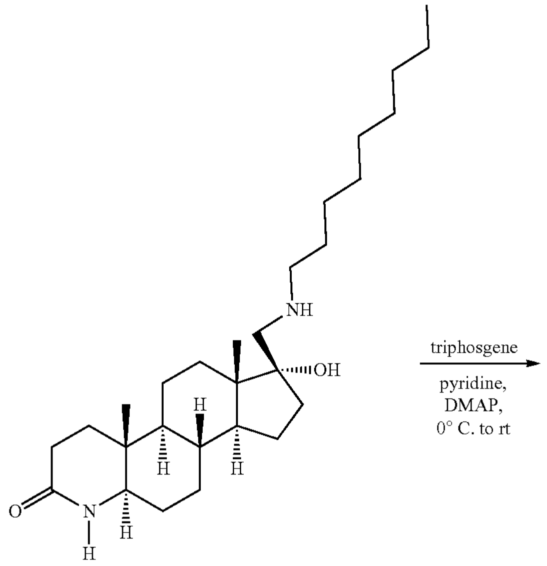

-continued

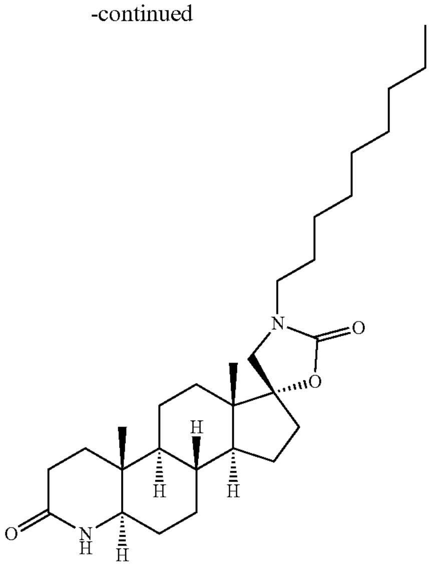

INH-464

(4aR,4bS,6aS,7R,9aS,9bR,11aR)-4a,6a-dimethyl-3'-nonyltetradecahydrospiro [indeno[5,4-f]quinoline-7,5'-oxazolidine]-2,2'(1H)-dione (INH 464): To an ice cooled solution of N-nonylamino-4-azasteroid (84 mg, 0.18 mmol) in pyridine (5 ml) was added DMAP (2 mg) and triphosgene (80 mg, 0.27 mL). The cooling bath was subsequently removed and the resulting mixture was stirred at rt for 10 h. The reaction mixture was then poured into ice and extracted with DCM. The organic extracts were washed with brine and dried with sodium sulfate. After evaporation, the crude compound was purified by flash chromatography with DCM/MeOH (99:1) to yield 60 mg (69% yield) of INH 464 as a yellowish solid. $^1$HNMR (400 MHz, $CDCl_3$) δ=5.39 (s, 1H, NH), 3.48 (d, J=9.2 Hz, 1H, $N—CH_2$), 3.25 (d, J=9.2 Hz, 1H, $N—CH_2$), 3.22 (t, J=7.4 Hz, 2H, $N—CH_2—CH_2$), 3.06 (dd, J=4.1 and 11.8 Hz, 1H, $H_5\alpha$), 2.47-2.33 (m, 2H), 2.18-2.11 (m, 1H), 1.96-1.22 (m, 26H), 1.06 (m, 1H), 0.90 (s, 3H), 0.88 (s, 3H), 0.87 (t, J=7.0 Hz, 3H, $CH_2—CH_3$), 0.72 (s, 3H). MS (APCI positive) m/z [M+H] 473.8. HPLC purity=95.3%.

Comparison of the Effect of Various INH7 Inhibitors on Cancer Cell Proliferation The effects of various inhibitors, including INH7-464, on MCF-7 cell proliferation over a period of 144 hours is illustrated in FIG. 1. The hormone source E1 (Estrone) was provided at 0.1 nM. Data are reported as % of DNA synthesis vs Control (0.1 nM E1) (100%). Quadruple wells were used for each condition and repeated in three independent experiments. Error bars represent SD. *, $P<0.05$ vs control; **, $P<0.001$ vs. control by Student's test. INH7-464 demonstrated the strongest inhibition on MCF-7 cell proliferation, showing significant inhibition at 2 μM.

The effect of INH7-10 and INH7-464 on both xenograft breast tumor cell models MCF-7 and T47D was further investigated. For the MCF-7 xenograft model, a decrease in the tumor size of more than 60%, relative to the control (E1), could be observed with both INH7-10 (59%±5%) and INH7-464 (60%±5%) on day 22. For the T47D xenograft model, a decrease in the tumor size of more than 51%, relative to the control (E1), could be observed with INH7-464 (51%±5%) on day 22. A decrease in the tumor size of more than 31%, relative to the control (E1), could be observed with INH7-10 (31%±6%) on day 22 for the T47D xenograft model. INH7-

464, thus demonstrates significant efficacy in reducing xenograft tumors induced by both MCF-7 and T47D breast cancer cell lines.

Toxicity Assay for INH7-464

Paclitaxel (PTX) was used as a reference compound and was dissolved in DMSO for the stock solutions. The stock solutions were subsequently diluted at multiple concentrations with culture media in order to obtain the final desired concentrations ranging from 1 nM-100 μM. The incubation time was 3 days. The $IC_{50}$ values (at which 50% of cell growth inhibition—concentration that inhibits 50% of cell proliferation—is observed) were calculated using an iterative least square regression method. The cytotoxicity values for the INH7-464 inhibitor were lower than those for Paclitaxel (PTX) in the different cell lines tested [581.6 nM (MCF-7); and 2669 nM (MCF-10A) respectively](cf. Table 3).

The toxicity of INH7-464 was subsequently evaluated in mice (8 mice/group) at various concentrations and was found to be very well tolerated after weekly subcutaneous injection at various concentrations (20-60 mg/kg) over a period of 21 days; there being no apparent toxicity at 60 mg/day/mouse (s.c.) (FIG. 10). Following the toxicity study, no significant weight changes could be observed for the liver, kidney, ovary and uterus (FIG. 11).

General Methods and Materials

Reagents and solvents were obtained from commercial suppliers (Sigma Aldrich, Strem, Combi-blocks, Alfa Aesar) and used without further purification, unless otherwise noted. All reactions that were moisture and air-sensitive were carried out in flame-dried glassware, under an argon atmosphere. Reaction progress was monitored by thin layer chromatography (TLC), using EMD silica gel 60 F254 aluminum plates. Spots were visualized with UV light (254 nm), followed by staining using a cerium ammonium molybdate (CAM) solution or a potassium-permanganate solution, followed by heating on a hot plate. SiliCycle® R10030B 230-400 mesh silica gel (Québec, QC, Canada) was used for flash chromatography. High-performance liquid chromatography (HPLC) analyses for chemical purities were performed on a Shimadzu Prominence instrument (Kyoto, Japan) using a diode array detector and an Altima C18 analytical reverse phase column. Nuclear magnetic resonance (NMR) spectra were recorded on a Bruker Avance 400 digital spectrometer (Billerica, MA, USA) at 400 MHz for $^{1}H$ NMR. The following abbreviations were used to designate multiplicities: s=singlet, d=doublet, t=triplet, q=quartet, quint=quintuplet, m=multiplet, br=broad. Low-resolution mass spectra (LRMS) were recorded on a Shimadzu Prominence instrument (Kyoto, Japan) equipped with a Shimadzu LCMS-2020 mass spectrometer and an APCI (atmospheric pressure chemical ionization) probe.

INH7-464 was administered by s.c. injection. INH7-464 was first dissolved in DMSO, followed by the addition of 0.4% methylcellulose to obtain a final 8% concentration of co-solvent (methylcellulose/DMSO (92/8). The injected volume was 0.1 mL (s.c.). The protocol was applied to 2 groups (8 mice/group), and divided-up as follows: Control Group: vehicle administrated weekly by s.c. injection of 0.4% methylcellulose/DMSO (92:8) for 3 weeks; INH7-464 Group: INH7-464 administrated weekly by s.c. injection (20, 30 and 60 mg/kg) for 3 consecutive weeks. All the mice were weighed every day. The liver, kidney, ovaries, and uterus were collected and weighed following 3 weeks of treatment.

Female athymic nude mice (4 weeks) were ovariectomized under isoflurane-induced anesthesia. One week after ovariectomy (OVX), $5\times10^{6}$ MCF-7 cells or $10\times10^{6}$ T47D cells suspended in a 100 ml mixture of Matrigel (BD)/culture medium (50:50) were administered by s.c. injection on both side of each mice. All mice were supplemented by daily s.c. injection 0.1 μg Estradiol (E2) for 5 weeks. Group 1—Control: E1 0.1 μg/mice/day; Group 2: E2 0.1 μg/mice/day; Group 3: OVX (Group of mice having had an ovariectomy); Group 4: E1 0.1 μg/mice/day; INH7(10) 5 mg/kg/day; Group 5: E1 0.1 μg/mice/day; INH7(464) 5 mg/kg/day. The animals were euthanized on day 23, followed by the collection of tumor specimens and blood samples. The estrogen-sensitive organs (uterus and vagina), liver and kidney were removed and excised of fat and weighed. Tumor specimens were photographed and weighed. E1: Estrone; E2: Estradiol; OVX: group of mice having had an ovariectomy—not treated with an INH7 inhibitor, but instead were subjected to daily subcutaneous (s.c.) injection with vehicle (0.4% methylcellulose/DMSO (92/8)).

All of the compounds and/or methods disclosed and claimed herein can be made and executed without undue experimentation in light of the present disclosure. While the compounds and methods of this disclosure have been described in terms of preferred embodiments, it will be apparent to those of skill in the art that variations may be applied to the compounds and/or methods and in the steps or in the sequence of steps of the methods described herein without departing from the concept, spirit and scope of the disclosure. More specifically, it will be apparent that certain agents which are chemically related may be substituted for the agents described herein while the same or similar results would be achieved. All such similar substitutes and modifications apparent to those skilled in the art are deemed to be within the spirit, scope and concept of the disclosure as defined by the appended claims.

TABLE 1

Effect of various inhibitors of 17b-HSD1 (INH7-10 and INH7-464) on the growth of human MCF-7 breast tumors in nude mice over a period of 22 days expressed as % of initial growth.

| Days | E1 | E2 | OVX | INH7 (10) | INH7 (464) |
|---|---|---|---|---|---|
| 0 | 100 | 100 | 100 | 100 | 100 |
| 5 | 102.886 | 82.8535 | 73.9924 | 95.5496 | 88.1406 |
| 9 | 100.227 | 97.2662 | 73.9721 | 78.5457 | 81.8741 |
| 12 | 109.033 | 131.541 | 83.8482 | 85.0172 | 84.2617 |
| 13 | 95.3089 | 123.252 | 69.3147 | 80.2823 | 66.5956 |
| 19 | 100.249 | 108.413 | 67.2073 | 71.1033 | 67.8843 |
| 22 | 102.648 | 120.974 | 48.2038 | 59.4114 | 59.6876 |

TABLE 2

| Effect of various inhibitors of 17b-HSD1 (INH7-10 and INH7-464) on the growth of human T47D breast tumors in nude mice over a period of 22 days expressed as % of initial growth. | | | | | |
|---|---|---|---|---|---|
| Days | E1 | E2 | OVX | INH7 (10) | INH7 (464) |
| 0 | 100 | 100 | 100 | 100 | 100 |
| 5 | 93.64 | 112.55 | 105.67 | 89.41 | 100.51 |
| 9 | 113.43 | 120.84 | 81.8141 | 98.79362 | 78.1158 |
| 12 | 112.0519 | 121.306 | 78.6751 | 80.3944 | 76.9139 |
| 15 | 122.0034 | 150.417 | 69.5895 | 87.12289 | 63.5165 |
| 19 | 112.9356 | 144.117 | 68.5695 | 80.2485 | 67.9195 |
| 22 | 112.831 | 138.919 | 67.985 | 75.3021 | 50.9558 |

TABLE 3

| Cytotoxicity of the INH7-464 inhibitor on the MCF-7 and MCF-10A cell lines. | | |
|---|---|---|
| Cytotoxicity | Paclitaxel (PTX) | INH7 (464) |
| $IC_{50}$ (MCF-7) | 3.082 nM | 581.6 nM |
| $IC_{50}$ (MCF-10A) | 0.6373 nM | 2669 nM |

REFERENCES

1. Bellavance, E.; The, V. L.; Poirier, D. *J. Med. Chem.* 2009, 52, 7488-7502.
2. Wang X. Q.; Gerard, C.; Theriault, J. F.; Poirier, D.; Doillon, C. J.; Lin, S. X. *J. Mol. Cell. Biol.* 2015, 7, 568-79.
3. Ayan, D.; Maltais, R.; Hospital, A.; Poirier, D. *Bioorg. Med. Chem.* 2014, 22: 5847-59.
4. Kenmogne, L. C.; Ayan, D.; Roy, J.; Maltais, R; Poirier, D. PLoS One. 2015, 10(12): e0144890.
5. Zhang, C. Y.; Wang, W. Q.; Chen J.; Lin, S. X., J. Steroid Biochem. Mot. Biol. 2015, 150, 24-34.

The invention claimed is:

1. A 17β-hydroxysteroid dehydrogenase 7 (17β-HSD7) inhibitor compound of Formula I:

Formula I

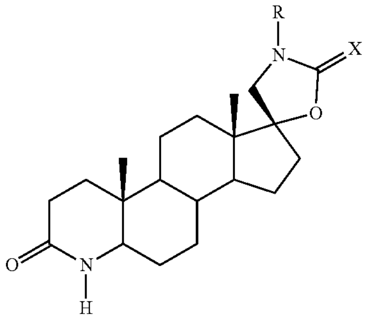

or a pharmaceutically acceptable salt or solvate thereof, wherein, R is $C_{\leq 12}$ alkyl or $C_{\leq 12}$ cycloalkyl; and X is O or S.

2. The inhibitor of claim 1, having the structure:

INH7-464

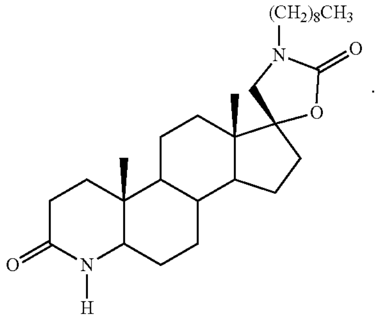

3. A method of treating breast cancer in a subject in need thereof, comprising administering to the subject, the 17β-HSD7 inhibitor compound of claim 1.

4. The method of claim 3, wherein the cancer is an estrogen-sensitive cancer.

5. The method of claim 3, further comprising treating the subject with a secondary cancer therapy.

6. The method of claim 5, wherein the secondary cancer therapy is selected from the group consisting of chemotherapy, toxin therapy, radiation therapy, hormone or anti-hormone therapy, surgery, cryotherapy, or immunotherapy.

7. The method of claim 3, further comprising administering the inhibitor at least a second time.

8. The method of claim 3, wherein the inhibitor is administered intravenously, intra-arterially, subcutaneously, topically, or intramuscularly.

9. The method of claim 3, wherein the inhibitor is administered systemically, regionally, locally or intratumorally.

10. The method of claim 3, wherein the cancer is multi drug resistant.

11. The method of claim 3, wherein the cancer is metastatic.

12. The method of claim 3, wherein the cancer is recurrent.

13. The method of claim 3, wherein treating comprises inhibiting cancer growth, killing cancer cells, reducing tumor burden, reducing tumor size, improving said subject's quality of life or prolonging said subject's length of life.

14. The method of claim 3, wherein the subject is a human.

15. The method of claim 3, wherein the subject is a non-human animal.

16. A pharmaceutical composition comprising a pharmaceutically acceptable amount of the inhibitor according to claim 1 and a pharmaceutically acceptable carrier.

17. A method of treating breast cancer in a subject in need thereof, comprising administering to the subject, the 17β-HSD7 inhibitor compound of claim 2.

18. The method of claim 17, wherein the cancer is an estrogen-sensitive cancer.

19. The method of claim 17, further comprising treating the subject with a secondary cancer therapy.

20. The method of claim 19, wherein the secondary cancer therapy is selected from the group consisting of chemotherapy, toxin therapy, radiation therapy, hormone or anti-hormone therapy, surgery, cryotherapy, or immunotherapy.

* * * * *